United States Patent [19]

Effland et al.

[11] Patent Number: 5,102,891
[45] Date of Patent: Apr. 7, 1992

[54] 1-(SUBSTITUTED PYRIDINYLAMINO)-1H-INDOL-5-YL SUBSTITUTED CARBAMATES

[75] Inventors: Richard C. Effland, Bridgewater; Larry Davis, Sergeantsville; Gordon E. Olsen, Somerset; Joseph T. Klein, Bridgewater; David G. Wettlaufer, Phillipsburg; Peter A. Nemoto, Bound Brook, all of N.J.

[73] Assignee: Hoechst-Roussel Pharmaceuticals Inc., Somerville, N.J.

[21] Appl. No.: 555,890

[22] Filed: Jul. 23, 1990

[51] Int. Cl.⁵ .................. A61K 31/47; C07D 401/14
[52] U.S. Cl. .................... 514/307; 514/212; 514/235.2; 514/253; 514/326; 514/333; 514/339; 540/597; 544/131; 544/364; 546/147; 546/256; 546/273
[58] Field of Search .............. 546/273, 156, 147, 194; 544/131, 364; 540/597; 514/307, 212, 235.2, 253, 326, 333, 339

[56] References Cited

U.S. PATENT DOCUMENTS

| | | | |
|---|---|---|---|
| 4,970,218 | 11/1990 | Effland et al. | 546/273 |
| 4,983,615 | 11/1991 | Effland et al. | 546/273 |
| 4,992,448 | 2/1991 | Effland et al. | 546/273 |
| 5,006,537 | 4/1991 | Effland et al. | 546/273 |

Primary Examiner—C. Warren Ivy
Assistant Examiner—James H. Turnipseed
Attorney, Agent, or Firm—Tatsuya Ikeda

[57] ABSTRACT

There are disclosed various compounds of the formula below,

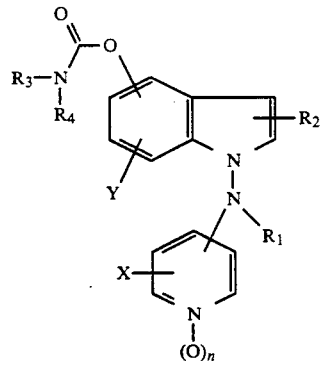

where
n is 0 or 1;
X is hydrogen, halogen, nitro, amino, trifluoromethyl, loweralkyl, or loweralkoxy;
Y is hydrogen, halogen, nitro, amino, trifluoromethyl, loweralkyl, or loweralkoxy;
$R_1$ is hydrogen, loweralkyl, arylloweralkyl, loweralkenyl, loweralkynyl, loweralkanoyl, arylloweralkanoyl, heteroarylloweralkyl or heteroarylloweralkanoyl;
$R_2$ is hydrogen, loweralkyl, formyl or cyano;
$R_3$ is hydrogen or loweralkyl;
$R_4$ is loweralkyl, arylloweralkyl, cycloalkyl, aryl or heteroaryl; or alternatively, —$NR_3R_4$ taken together constitutes

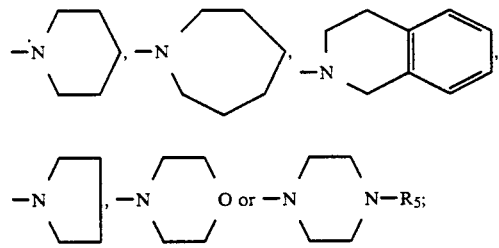

$R_5$ being hydrogen, loweralkyl, aryl, arylloweralkyl, heteroaryl or heteroarylloweralkyl, which compounds are useful for the treatment of various memory dysfunctions characterized by a cholinergic deficit such as Alzheimer's disease.

42 Claims, No Drawings

1-(SUBSTITUTED PYRIDINYLAMINO)-1H-INDOL-5-YL SUBSTITUTED CARBAMATES

The present invention relates to compounds of Formula I,

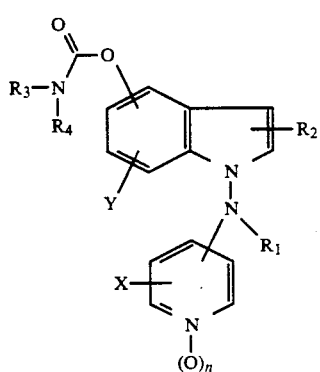
(I)

where n is 0 or 1;

X is hydrogen, halogen, nitro, amino, trifluoromethyl, loweralkyl, or loweralkoxy;

Y is hydrogen, halogen, nitro, amino, trifluoromethyl, loweralkyl, or loweralkoxy;

$R_1$ is hydrogen, loweralkyl, arylloweralkyl, loweralkenyl, loweralkynyl, loweralkanoyl, aryllower-alkanoyl, heteroarylloweralkyl or heteroarylloweralkanoyl;

$R_2$ is hydrogen, loweralkyl, formyl or cyano;

$R_3$ is hydrogen or loweralkyl;

$R_4$ is loweralkyl, arylloweralkyl, cycloalkyl, aryl or heteroaryl; or alternatively, —$NR_3R_4$ taken together constitutes

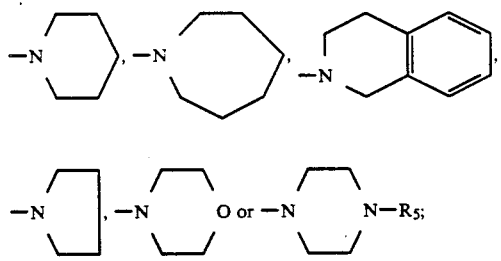

$R_5$ being hydrogen, loweralkyl, aryl, arylloweralkyl, heteroaryl or heteroarylloweralkyl, which compounds are useful for the treatment of various memory dysfunctions characterized by a cholinergic deficit such as Alzheimer's disease.

Also included within the scope of this invention are compounds depicted by the formula below where the group Z is hydrogen, loweralkyl or benzyl, and other parameters are as defined above, which are useful as direct precursors to the target compounds of this invention having Formula I.

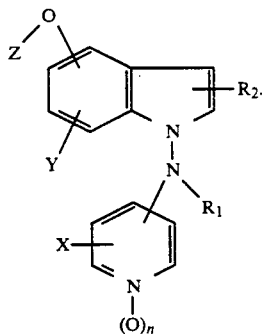

Unless otherwise stated or indicated, the following definitions shall apply throughout the specification and the appended claims.

The term loweralkyl shall mean a straight or branched alkyl group having from 1 to 8 carbon atoms. Examples of said loweralkyl include methyl, ethyl, n-propyl, iso-propyl, n-butyl, iso-butyl, sec-butyl, t-butyl and straight- and branched-chain pentyl, hexyl, heptyl and octyl.

The term cycloalkyl shall mean a cycloalkyl group of 3 to 7 carbon atoms.

The term halogen shall mean fluorine, chlorine, bromine or iodine.

The term aryl shall mean a phenyl group substituted with 0, 1 or 2 substituents which of each being independently loweralkyl, loweralkoxy, halogen or trifluoromethyl.

The term heteroaryl shall mean furanyl, thienyl, pyrrolyl or pyridinyl.

Throughout the specification and the appended claims, a given chemical formula or name shall encompass all stereo and tautomeric isomers where such isomers exist.

The compounds of this invention are prepared by utilizing one or more of the synthetic steps described below.

Throughout the description of the synthetic steps, the notations n, X, Y and $R_1$ through $R_5$ shall have the respective meanings given above unless otherwise stated or indicated.

STEP A

A benzyloxyaniline depicted below is allowed to react with $NaNO_2$ in a routine manner known to the art to afford the corresponding diazonium compound and the latter is reduced with $SnCl_2$ to afford the corresponding hydrazine compound, and thereafter the latter is allowed to react with the diethylacetal of propionaldehyde to afford the compound of Formula II. For details of the last reaction (Fisher indole synthesis), the reader is referred, for instance, to D. Keglevie et al., Chem. Absts. 56, 4710h.

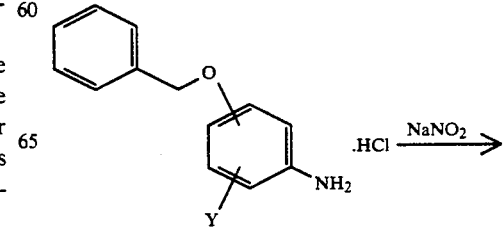

-continued

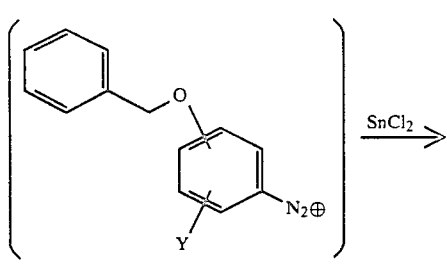

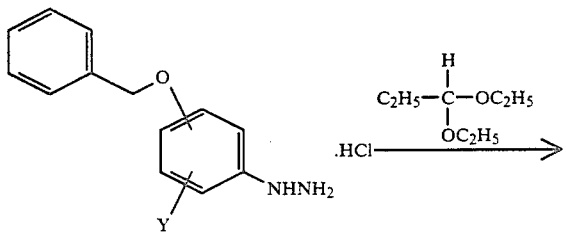

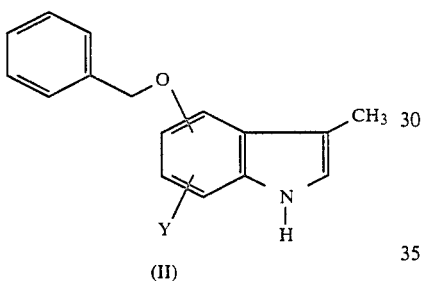

(II)

Where the 2-methylisomer of Compound II is desired, the above reaction is conducted in substantially the same manner as described above except that acetone is used instead of diethylacetal of propionaldehyde.

STEP B

A compound of Formula III where $R_2'$ is hydrogen or methyl is allowed to react with hydroxylamine-O-sulfonic acid in a routine manner known to the art to afford a compound of Formula IV. The starting compound of Formula III where $R_2'$ is hydrogen is either available on the market or can be synthesized from known compounds according to methods known to the art.

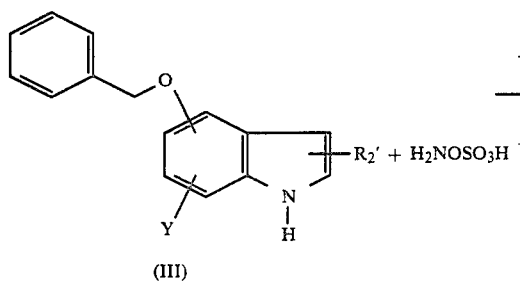

(III)

-continued

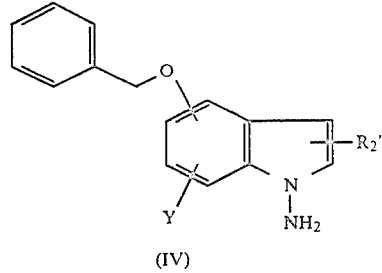

(IV)

STEP C

Compound IV is allowed to react with a halopyridine hydrochloride depicted below to afford a compound of Formula V. This reaction is typically conducted in a suitable solvent such as N-methyl-2-pyrrolidinone at a temperature of 20° to 200° C.

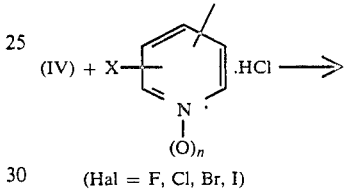

(Hal = F, Cl, Br, I)

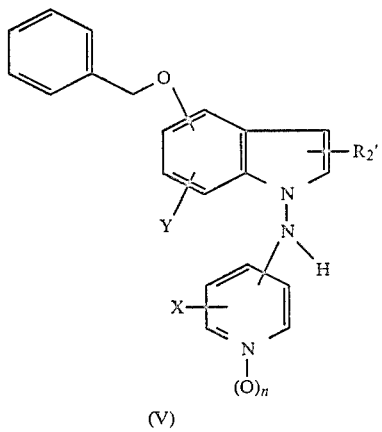

(V)

STEP D

Compound V is allowed to react with a suitable base, such as sodium hydride or potassium t-butoxide, and the resultant anion is allowed to react with a halide of the formula $R_1'$—Hal where $R_1'$ is loweralkyl, arylloweralkyl, loweralkenyl, loweralkynyl, loweralkanoyl, arylloweralkanoyl, heteroarylloweralkyl or heteroarylloweralkanoyl, and Hal is chlorine, bromine or iodine, or with a diloweralkylsulfate of the formula $R_1'$—O—SO$_2$—O—$R_1'$ where $R_1'$ is loweralkyl, in a routine manner known to the art to afford a compound of Formula VI.

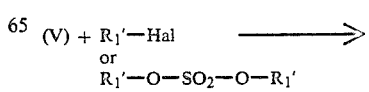

-continued

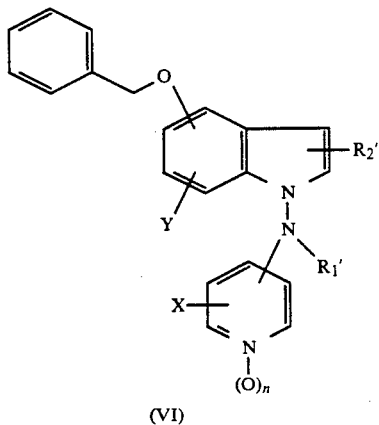

(VI)

STEP E

A compound of Formula VIa is allowed to react with phosphorus oxychloride and dimethylformamide in a routine manner known to the art to afford a compound of Formula VII.

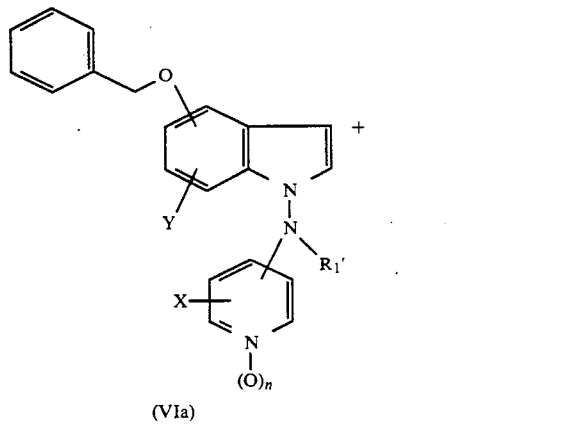

(VIa)

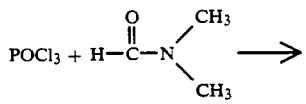

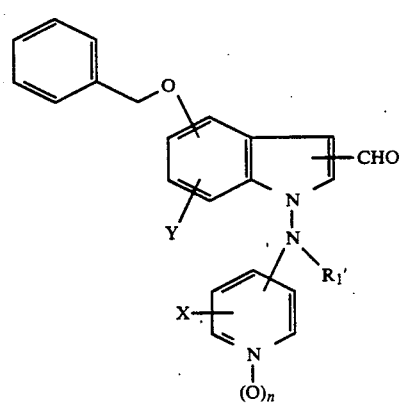

(VII)

STEP F

Compound VII is subjected to a Wittig reaction with an ylide of the formula

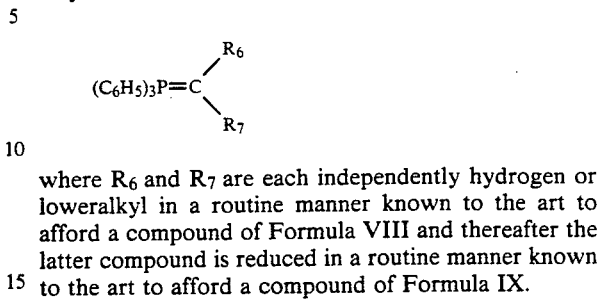

where $R_6$ and $R_7$ are each independently hydrogen or loweralkyl in a routine manner known to the art to afford a compound of Formula VIII and thereafter the latter compound is reduced in a routine manner known to the art to afford a compound of Formula IX.

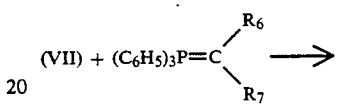

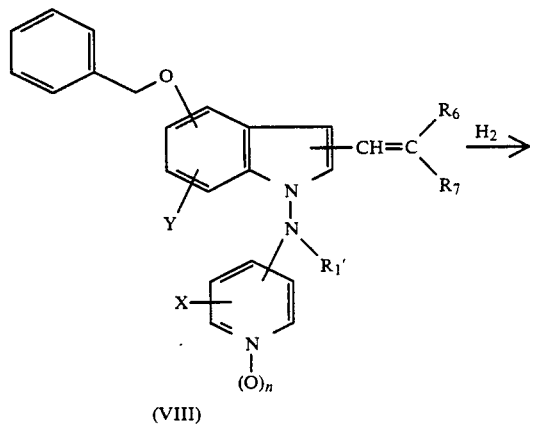

(VIII)

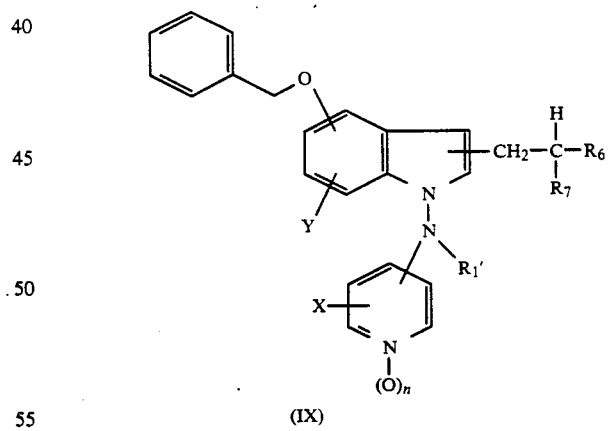

(IX)

STEP G

Compound VII is allowed to react with hydroxylamine in a routine manner known to the art to afford a corresponding oxime and the latter is allowed to react with benzenesulfonyl chloride to afford a nitrile compound of Formula X. The second step is typically conducted in a suitable solvent such as tetrahydrofuran or p-dioxane at a temperature of about 60° to 100° C.

-continued (X)

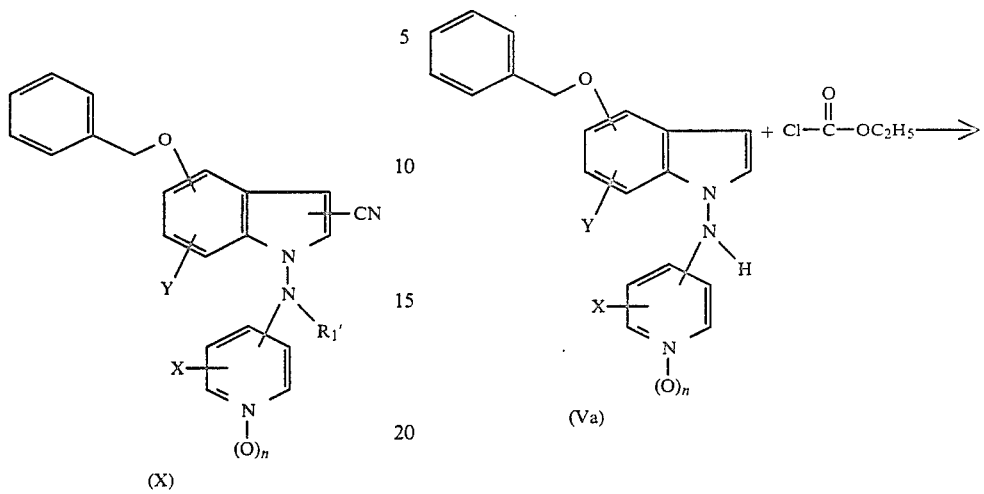

(Va)

STEP H

In order to prepare a compound of Formula XI depicted below where $R_2$ is not hydrogen or methyl, it is convenient to adopt the following procedure.

(XI)

($R_2 \neq$ H or CH$_3$)

Thus, a compound of Formula Va is allowed to react with ethyl chloroformate in a routine manner known to the art to afford an ethyl carbamate of Formula XII and thereafter the latter compound is subjected to one or more of STEPS E through G to afford a compound of Formula XIII. Subsequently, Compound XIII is hydrolyzed in a routine manner known to the art to afford Compound XI.

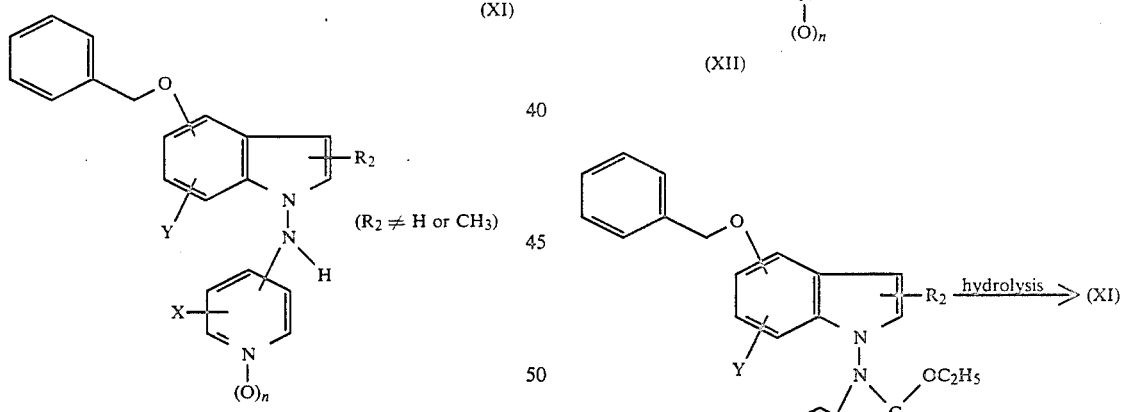

(XII)

(XIII)

STEP I

A compound of Formula XIV obtained from one of the foregoing STEPS is subjected to hydrogenolysis conducted in a routine manner known to the art to afford a compound of Formula XV.

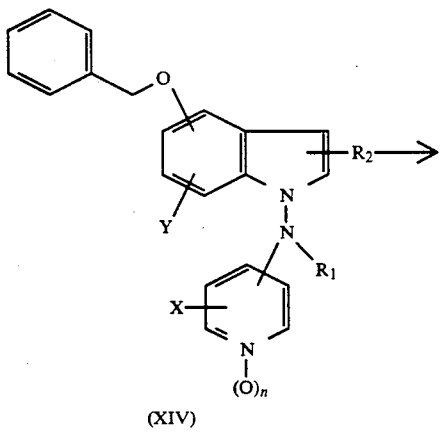

(XIV)

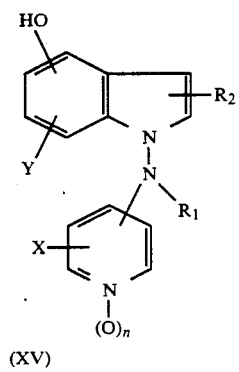

(XV)

In each of the foregoing STEPS A through I, the reactant molecule carries a benzyloxy group on the benzene portion thereof. However, the same reactions can also be accomplished in substantially the same manner as described above where the reactant molecule carries a loweralkoxy group instead of a benzyloxy group on the benzene portion thereof, except that in the case of STEP I, a cleavage reaction is utilized instead of hydrogenolysis. Said cleavage reaction is conducted in a routine manner known to the art, for instance, with the aid of 48% HBr, boron tribromide etherate, trimethylsilyl iodide or the sodium salt of ethyl mercaptan.

STEP J

Compound XV is allowed to react with 1,1'-carbonyldiimidazole and the resultant reaction product is allowed to react with an amine of the formula

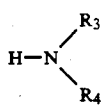

in a routine manner known to the art to afford Compound I.

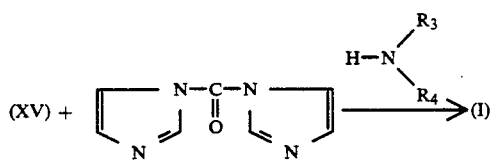

Typically, the first step is conducted in a suitable solvent such as tetrahydrofuran at room temperature. Typically, the second step is conducted by adding a suitable amount of the desired amine in glacial acetic acid to the reaction mixture.

Alternatively, where Compound I in which the group $R_3$ is hydrogen is desired, Compound XV is allowed to react with an isocyanate of the formula $R_4$—NCO in a routine manner known to the art to afford Compound I.

(XV)+$R_4$—NCO→(I) ($R_3$=H)

The compounds of Formula I of the present invention are useful for the treatment of various memory dysfunctions characterized by a decreased cholinergic function such as Alzheimer's disease.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. We have determined in vitro inhibition of acetylcholinesterase activity in rat striatum.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, smooth muscle, various glands and red blood cells. AChE may be distinguished from other cholinesterases by substrate and inhibitor specificities and by regional distribution. Its distribution in brain roughly correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying cholinesterase activity. This is a modification of the method of Ellman et al., Biochem. Pharmacol. 7,88 (1961).

Procedure

A. Reagents 1. 0.05M Phosphate buffer, pH 7.2
   (a) 6.85 g $NaH_2PO_4.H_2O$/100 ml distilled $H_2O$
   (b) 13.40 g $Na_2HPO_4.7H_2O$/100 ml distilled $H_2O$
   (c) add (a) to (b) until pH reaches 7.2
   (d) Dilute 1:10
2. Substrate in buffer
   (a) 198 mg acetylthiocholine chloride (10 mM)
   (b) q.s. to 100 ml with 0.05M phosphate buffer, pH 7.2 (reagent 1)
3. DTNB in buffer
   (a) 19.8 mg 5,5-dithiobisnitrobenzoic acid (DTNB) (0.5 mM)

(b) q.s. to 100 ml with 0.05M phosphate buffer, pH 7.2 (reagent 1)

4. A 2 mM stock solution of the test drug is made up in a suitable solvent and q.s. to volume with 0.5 mM DTNB (reagent 3). Drugs are serially diluted (1:10) such that the final concentration (in cuvette) is $10^{-4}$M and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 25 microliter aliquot of the homogenate is added to 1.0 milliter vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)
Program #6 Kindata:
Source—Vis
Wavelength—412 nm
Sipper—none
Cuvettes—2 ml cuvettes using auto 6-sampler
Blank—1 for each substrate concentration
Interval time—15 seconds (15 or 30 seconds for kinetics)
Total time—5 minutes (5 or 10 minutes for kinetics)
Plot—yes
Span—autoscale
Slope—increasing
Results—yes (gives slope)
Factor—1

Reagents are added to the blank and sample cuvettes as follows:

| | |
|---|---|
| Blank: | 0.8 ml Phosphate Buffer/DTNB |
| | 0.8 ml Buffer/Substrate |
| Control: | 0.8 ml Phosphate Buffer/DTNB/Enzyme |
| | 0.8 ml Phosphate Buffer/Substrate |
| Drug: | 0.8 ml Phosphate Buffer/DTNB/Drug/Enzyme |
| | 0.8 ml Phosphate Buffer/Substrate |

Blank values are determined for each run to control for non-enzymatic hydrolysis of substrate and these values are automatically subtracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM yielding 0.25 mM final concentration.

$$\% \text{ Inhibition} = \frac{\text{slope control} - \text{slope drug}}{\text{slope control}} \times 100$$

$IC_{50}$ values are calculated from log-probit analysis

Results of this assay for some of the compounds of this invention and physostigmine (reference compound) are presented in Table 1.

TABLE 1

| Compound | Inhibitory Concentration ($\mu$M) Brain AChE |
|---|---|
| 1-(propyl-4-pyridinylamino)-1H-indol-5-yl methylcarbamate | 0.0023 |
| (S)-(−)-1-(propyl-4-pyridinyl-amino)-1H-indol-5-yl 1-phenylethylcarbamate | 30.21 |
| Physostigmine | 0.006 |

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and those for tacrine and pilocarpine (reference compounds) are presented in Table 2.

TABLE 2

| Compound | Dose (mg/kg of body weight, s.c) | % of Animals with Scopolamine Induced Memory Deficit Reversal |
|---|---|---|
| 1-(propyl-4-pyridinyl-amino)-1H-indol-5-yl methylcarbamate | 0.35 | 21 |
| Tacrine | 0.63 | 13 |
| Pilocarpine | 5.0 | 13 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
1-(Propyl-4-pyridinylamino)-1H-indol-5-yl methylcarbamate;
1-(Propyl-4-pyridinylamino)-1H-indol-5-yl ethylcarbamate;
1-(Propyl-4-pyridinylamino)-1H-indol-5-yl propylcarbamate;
1-(Propyl-4-pyridinylamino)-1H-indol-5-yl isopropylcarbamate;
1-(Propyl-4-pyridinylamino)-1H-indol-5-yl butylcarbamate;
1-(Propyl-4-pyridinylamino)-1H-indol-5-yl cyclohexylcarbamate;
1-(Propyl-4-pyridinylamino)-1H-indol-5-yl phenylmethylcarbamate;
1-(Propyl-4-pyridinylamino)-1H-indol-5-yl 2-phenylethylcarbamate;
(S)-(−)-1-(Propyl-4-pyridinylamino)-1H-indol-5-yl 1-phenylethylcarbamate;
1-[(3-Fluoro-4-pyridinyl)propylamino]-1H-indol-5-yl methylcarbamate;
1-[(3-Fluoro-4-pyridinyl)propylamino]-1H-indol-5-yl butylcarbamate;
1-[(3-Fluoro-4-pyridinyl)propylamino]-1H-indol-5-yl heptylcarbamate;
1-(Methyl-4-pyridinylamino)-1H-indol-5-yl butylcarbamate;
1-(Methyl-4-pyridinylamino)-1H-indol-5-yl methylcarbamate;
1-(Methyl-4-pyridinylamino)-1H-indol-5-yl phenylmethylcarbamate;
3-Methyl-1-(propyl-4-pyridinylamino)-1H-indol-5-yl methylcarbamate;
1-[(3-Fluoro-4-pyridinyl)propylamino]-3-methyl-1H-indol-5-yl methylcarbamate;
3-Methyl-1-(propyl-4-pyridinylamino)-1H-indol-5-yl butylcarbamate;
1-[(3-Fluoro-4-pyridinyl)propylamino]-3-methyl-1H-indol-5-yl butylcarbamate;
1-(Propyl-4-pyridinylamino)-1H-indol-5-yl heptylcarbamate;
1-(Propyl-4-pyridinylamino)-1H-indol-5-yl 1,2,3,4-tetrahydro-2-isoquinolinylcarbamate;
1-(Propyl-4-pyridinylamino)-1H-indol-5-yl piperidinylcarbamate;
1-(Propyl-4-pyridinylamino)-1H-indol-5-yl 4-chlorophenylmethylcarbamate;
1-(Propyl-4-pyridinylamino)-1H-indol-5-yl dimethylcarbamate;
1-[(3-Fluoro-4-pyridinyl)propylamino]-3-methyl-1H-indol-5-yl heptylcarbamate;
1-[(3-Fluoro-4-pyridinyl)propylamino]-3-methyl-1H-indol-5-yl phenylmethylcarbamate;
1-[(3-Fluoro-4-pyridinyl)propylamino]-3-methyl-1H-indol-5-yl 1,2,3,4-tetrahydro-2-isoquinolinylcarbamate;
3-Methyl-1-(propyl-4-pyridinylamino)-1H-indol-5-yl heptylcarbamate;
3-Methyl-1-(propyl-4-pyridinylamino)-1H-indol-5-yl 1,2,3,4-tetrahydro-2-isoquinolinylcarbamate;
3-Methyl-1-(propyl-4-pyridinylamino)-1H-indol-5-yl phenylmethylcarbamate;
1-[Methyl-(3-methyl-4-pyridinyl)amino]-1H-indol-5-yl methylcarbamate;
1-(Methyl-4-pyridinylamino)-1H-indol-5-yl 4-phenylpiperazin-1-ylcarbamate;
1-(Methyl-4-pyridinylamino)-1H-indol-5-yl morpholin-4-ylcarbamate;

1-(Propyl-4-pyridinylamino)-1H-indol-5-yl methylcarbamate N-oxide;
1-(Methyl-4-pyridinylamino)-5-phenylmethoxy-1H-indole;
1-(Methyl-4-pyridinylamino)-1H-indol-5-ol;
3-Methyl-1-(propyl-4-pyridinylamino)-1H-indol-5-ol;
3-Methyl-5-(phenylmethoxy)-1-(4-pyridinylamino)-1H-indole;
3-Methyl-5-(phenylmethoxy)-1-(propyl-4-pyridinylamino)-1H-indole;
1-[(3-Fluoro-4-pyridinyl)propylamino]-3-methyl-5-(phenylmethoxy)-1H-indole;
1-[(3-Fluoro-4-pyridinyl)propylamino]-3-methyl-1H-indol-5-ol;
3-Methyl-1-(4-pyridinylamino)-1H-indol-5-ol;
1-(3-Methyl-4-pyridinylamino)-5-phenylmethoxy-1H-indole;
1-[Methyl-(3-methyl-4-pyridinyl)amino]-5-phenylmethoxy-1H-indole;
1-[Methyl-(3-methyl-4-pyridinyl)amino]-1H-indol-5-ol;
1-(Methyl-4-pyridinylamino)-5-phenylmethoxy-1H-indol-3-carboxaldehyde;
3-Cyano-1-(methyl-4-pyridinylamino)-5-phenylmethoxy-1H-indole;
1-(2-Phenylethyl-4-pyridinylamino)-1H-indol-5-ol; and
1-(2-Propynyl-4-pyridinylamino)-5-phenylmethoxy-1H-indole;

Examples of this invention are presented below.

EXAMPLE 1

5-Phenylmethoxy-1H-indole-1-amine

To 5-phenylmethoxyindole (50 g) in 300 ml of dimethylformamide at ice bath temperature was added milled potassium hydroxide (62.72 g). Then hydroxylamine-O-sulfonic acid (32.93 g) was added portionwise, keeping the internal temperature below 20° C. After the addition was complete, the mixture was stirred for one hour, then poured into water and extracted with ethyl acetate. The organic layer was washed with water and dried (sat. NaCl, anhy. MgSO4). After filtration, the solvent was evaporated to yield an oil (71 g), which was eluted with dichloromethane on silica gel columns via HPLC. The desired fractions were concentrated to yield a solid (21.15 g). Of this material, 3.0 g was triturated with ether to yield a solid, 2.4 g, m.p. 126°-128° C.

ANALYSIS: Calculated for $C_{15}H_{14}N_2O$: 75.60% C; 5.92% H; 11.76% N. Found: 75.54% C; 5.97% H; 11.87% N.

EXAMPLE 2

5-Phenylmethoxy-1-(4-pyridinylamino)-1H-indole

To 250 ml of N-methyl-2-pyrrolidinone was added 5-(phenylmethoxy)-1H-indole-1-amine (29.7 g) and the solution was heated to 80° C. Then 4-chloropyridine hydrochloride (20.55 g) was added portionwise and the mixture was stirred for three hours, cooled, poured into water, basified with aqueous sodium carbonate and extracted with toluene. The organic/aqueous mixture was filtered to yield a solid (39 g), which was triturated with ether to yield a solid (27 g). Of this material, 3.0 g was eluted with 5% methanol/dichloromethane on a silica gel column via HPLC. The desired fractions were concentrated to yield a solid, 2.5 g, m.p. 143°-145° C.

ANALYSIS: Calculated for $C_{20}H_{17}N_3O$: 76.17% C; 5.44% H; 13.32% N. Found: 75.82% C; 5.43% H; 13.21% N.

EXAMPLE 3

1-(4-Pyridinylamino)-1H-indol-5-ol

To 0.8 g of 10% palladium on carbon in 10 ml of absolute ethanol was added a solution of 5-(phenylmethoxy)-1-(4-pyridinylamino)-1H-indole (4.0 g) in 240 ml of absolute ethanol and this was hydrogenated on a Parr apparatus for four hours at 50° C. at 50 psig $H_2$. The mixture was cooled and filtered, and the filtrate was concentrated to yield an oil (4.2 g), which was eluted with ethyl acetate on a silica gel column via HPLC. The desired fractions were concentrated to yield an oil (3.72 g). This material was eluted with 10% methanol/dichloromethane on a silica gel column via HPLC. The desired fractions were concentrated to yield a foam (1.8 g), which was recrystallized from ethyl acetate to yield a solid (1.5 g), m.p. 232°-234° C.

ANALYSIS: Calculated for $C_{13}H_{11}N_3O$: 69.32% C; 4.92% H; 18.66% N. Found: 69.16% C; 4.76% H; 18.52% N.

EXAMPLE 4

1-(Methyl-4-pyridinylamino)-5-phenylmethoxy-1H-indole hydrochloride 5-(Phenylmethoxy)-1-(4-pyridinylamino)-1H-indole (25 g) was slowly added to an ice-cooled solution of potassium tert-butoxide (11 g) in 250 mL tetrahydrofuran. Following the anion formation, a solution of dimethyl sulfate (12 g) in 25 mL tetrahydrofuran was slowly added so that the internal reaction temperature remained below 10° C. After one hour, the reaction mixture was stirred with water and extracted with ether. The organic layer was washed with water and saturated sodium chloride solution and thereafter dried (anhydrous magnesium sulfate), filtered and concentrated to afford a solid, 28 g. This solid was eluted through silica with 5% methanol in dichloromethane via HPLC to yield 22 g of a solid, m.p. 118°-121° C. An analytical sample was prepared by converting 1.5 g to the hydrochloride salt in methanol/ether to yield 1.5 g of crystals, m.p. 235°-236° C. (dec.).

ANALYSIS: Calculated for $C_{21}H_{20}ClN_3O$: 68.94% C; 5.51% H; 11.49% N. Found: 68.60% C; 5.50% H; 11.28% N.

EXAMPLE 5

1-(Methyl-4-pyridinylamino)-1H-indol-5-ol

A solution of 1-(methyl-4-pyridinylamino)-5-phenylmethoxy-1H-indole (9 g) in 250 mL ethanol containing 0.6 g 10% palladium on activated charcoal was hydrogenated at 50 psi at 50° C. for three hours via Parr hydrogenation apparatus. After cooling, the mixture was filtered through Celite and concentrated. The residue was eluted through silica with 5% methanol in dichloromethane via flash column chromatography to yield 6.2 g solid. A three gram portion was recrystallized from acetonitrile to yield 2.6 g solid, m.p. 191°-193° C. This was again recrystallized from acetonitrile to yield 2.2 g crystals, m.p. 192°-193° C.

ANALYSIS: Calculated for $C_{14}H_{13}N_3O$: 70.27% C; 5.48% H; 17.57% N. Found: 69.96% C; 5.39% H; 17.53% N.

EXAMPLE 6

1-(Methyl-4-pyridinylamino)-1H-indol-5-yl methylcarbamate

Methyl isocyanate (0.72 g) was added to a solution of 1-(methyl-4-pyridinylamino)-1H-indol-5-ol (2.5 g) in 75 mL tetrahydrofuran containing milled potassium carbonate (2 g). After stirring three hours at ambient temperature the mixture was filtered and concentrated. The residue was eluted through silica with ethyl acetate via flash column chromatography to yield a solid 3.1 g. This was eluted through silica with 5% methanol in dichloromethane via HPLC to yield 2.6 g solid, m.p. 186°–188° C. This was recrystallized from 20% methanol in ether to yield 1.6 g of product, m.p. 186°–188° C.

ANALYSIS: Calculated for $C_{16}H_{16}N_4O_2$: 64.85% C; 5.44% H; 18.91% N. Found: 64.85% C; 5.58% H; 18.73% N.

EXAMPLE 7

1-(Methyl-4-pyridinylamino)-1H-indol-5-yl butylcarbamate hydrochloride

Butyl isocyanate (1.2 g) was added to a solution of 1-(methyl-4-pyridinylamino)-1H-indol-5-ol (2.5 g) in 75 mL tetrahydrofuran containing potassium carbonate (milled, 2 g). After stirring twenty hours at ambient temperature, the mixture was filtered and concentrated. The residue was eluted through silica with ethyl acetate via flash column chromatography to yield 3.7 g solid, m.p. 108°–111° C. This was converted to the hydrochloride salt in methanol/ether to yield 3.3 g crystals, m.p. 232°–234° C. (dec.).

ANALYSIS: Calculated for $C_{19}H_{22}N_4O_2.HCl$: 60.87% C; 6.18% H; 14.95% N. Found: 60.89% C; 6.34% H; 14.88% N.

EXAMPLE 8

1-(Methyl-4-pyridinylamino)-1H-indol-5-yl phenylmethylcarbamate

Benzyl isocyanate (1.7 g) was added to a solution of 1-(methyl-4-pyridinylamino)-1H-indol-5-ol (2.5 g) in 75 mL tetrahydrofuran containing potassium carbonate (milled, 3 g). After stirring three hours at ambient temperature the mixture was filtered and concentrated. The residue was eluted through silica with ethyl acetate via flash column chromatography to yield 3.8 g solid. This was recrystallized from acetonitrile to yield 3.2 g crystals, m.p. 179°–181° C.

ANALYSIS: Calculated for $C_{22}H_{20}N_4O_2$: 70.95% C; 5.41% H; 15.05% N. Found: 70.67% C; 5.35% H; 15.12% N.

EXAMPLE 9

1-(Propyl-4-pyridinylamino)-5-phenylmethoxy-1H-indole maleate

To potassium tert-butoxide (2.80 g) in 20 ml of tetrahydrofuran cooled to ice bath temperature was added dropwise a solution of 5-phenylmethoxy-1-(4-pyridinylamino)-1H-indole (6.5 g) in 60 ml of tetrahydrofuran. This mixture was stirred for 10 minutes and then a solution of 1-bromopropane (3.08 g) in 10 ml of tetrahydrofuran was added dropwise. The reaction was allowed to proceed for three hours at room temperature. The mixture was then poured into water and extracted with ethyl acetate. The organic layer was washed with water and dried (sat. NaCl, anhy. MgSO$_4$). After filtration, the solvent was removed to yield an oil (8.5 g) which was eluted with ethyl acetate on a silica gel column via HPLC. The desired fractions were concentrated to yield an oil (5.5 g). Of this material 1.0 g was dissolved in methanol and acidified with a methanol solution of maleic acid. After diluting with ether, the precipitate was collected to yield a solid 1.0 g, m.p. 118°–119° C.

ANALYSIS: Calculated for $C_{23}H_{23}N_3O.C_4H_4O_4$: 68.48% C; 5.75% H; 8.87% N. Found: 68.29% C; 5.72% H; 8.86% N.

EXAMPLE 10

1-(Propyl-4-pyridinylamino)-1H-indol-5-ol

To 0.3 g of 10% Pd/C in 10 ml of absolute ethanol was added 5-phenylmethoxy-1-(propyl-4-pyridinylamino)-1H-indole (3.0 g) in 240 ml of ethanol and this was hydrogenated on a Parr apparatus for 48 hours at 50° C. and 50 psig H$_2$. The reaction mixture was then filtered and the filtrate concentrated to yield an oil (2.2 g), which was eluted with 5% methanol/dichloromethane on a silica gel column via HPLC. The desired fractions were concentrated to yield a solid (1.8 g) which was recrystallized from methanol/ether (1:1) to yield a solid 1.6 g, m.p. 214°–216° C.

ANALYSIS: Calculated for $C_{16}H_{17}N_3O$: 71.89% C; 6.41% H; 15.72% N. Found: 71.78% C; 6.41% H; 15.61% N.

EXAMPLE 11

1-(Propyl-4-pyridinylamino)-1H-indol-5-yl methylcarbamate

To 2.5 g of 1-(propyl-4-pyridinylamino)-1H-indol-5-ol in 30 ml of tetrahydrofuran was added potassium carbonate (milled, 1.3 g) followed by methyl isocyanate (0.56 ml). The reaction was allowed to proceed for half an hour. The reaction mixture was then filtered and the filtrate concentrated to yield a solid (2.9 g) which was eluted with 5% methanol in dichloromethane on a silica gel column via HPLC. The desired fractions were concentrated to yield a solid (2.7 g) which was recrystallized from isopropyl ether to yield a solid 1.8 g, m.p. 158°–159° C.

ANALYSIS: Calculated for $C_{18}H_{20}N_4O_2$: 66.65% C; 6.22% H; 17.27% N. Found: 66.83% C; 6.10% H; 17.18% N.

EXAMPLE 12

1-(Propyl-4-pyridinylamino)-1H-indol-5-yl ethylcarbamate hydrochloride

Ethyl isocyanate (1 g) was added to a solution of 1-(propyl-4-pyridinylamino)-1H-indol-5-ol (3.3 g) in 75 mL of tetrahydrofuran containing potassium carbonate (milled, 2 g). After stirring twenty hours at ambient temperature, the mixture was filtered and the filtrate was concentrated. The residue was eluted through silica with ethyl acetate via flash column chromatography to yield 4.5 g of the product as a solid, m.p. 139°–141° C. This was converted to the hydrochloride salt in methanol/ether to yield 4.3 g of crystals, m.p. 209°–211° C. (dec.).

ANALYSIS: Calculated for $C_{19}H_{22}N_4O_2.HCl$: 60.87% C; 6.18% H; 14.95% N. Found: 60.81% C; 6.16% H; 14.84% N.

EXAMPLE 13

1-(Propyl-4-pyridinylamino)-1H-indol-5-yl propylcarbamate

To a solution of 1-(propyl-4-pyridinylamino)-1H-indol-5-ol (2.1 g) in 50 ml of tetrahydrofuran was added potassium carbonate (milled, 1.3 g). Then propyl isocyanate (0.67 g) was added and the reaction mixture was stirred for 2 hours. The mixture was filtered and the filtrate was concentrated to yield an oil (2.8 g), which was eluted with 5% methanol/dichloromethane on a silica gel column via HPLC. The desired fractions were concentrated to yield an oil which solidified on standing (2.5 g), m.p. 120°–122° C.

ANALYSIS: Calculated for $C_{20}H_{24}N_4O_2$: 68.16% C; 6.86% H; 15.90% N. Found: 67.87% C; 6.89% H; 15.93% N.

EXAMPLE 14

1-(Propyl-4-pyridinylamino)-1H-indol-5-yl isopropylcarbamate

To a solution of 1-(propyl-4-pyridinylamino)-1H-indol-5-ol (2.1 g) in 50 ml of tetrahydrofuran was added potassium carbonate (milled, 1.3 g). Then isopropyl isocyanate (0.67 g) was added and the reaction mixture was stirred for 4 hours. The mixture was filtered and the filtrate was concentrated to yield a solid (3.2 g), which was eluted with 5% methanol/dichloromethane on a silica gel column via HPLC. The desired fractions were concentrated to yield an oil which solidified on standing (2.75 g), m.p. 131°–133° C.

ANALYSIS: Calculated for $C_{20}H_{24}N_4O_2$: 68.16% C; 6.86% H; 15.90% N. Found: 68.16% C; 6.84% H; 15.84% N.

EXAMPLE 15

1-(Propyl-4-pyridinylamino)-1H-indol-5-yl butylcarbamate hydrochloride

Butyl isocyanate (1.3 g) was added to a solution of 1-(propyl-4-pyridinylamino)-1H-indol-5-ol (3.3 g) in 75 mL tetrahydrofuran containing potassium carbonate (milled, 2 g). After stirring twenty hours at ambient temperature, the mixture was filtered and the filtrate was concentrated. The residue was eluted through silica with ethyl acetate via flash column chromatography to yield 5 g of the product as an oil. This material was converted to the hydrochloride salt in methanol/ether to yield 4 g of crystals, m.p. 178°–180° C.

ANALYSIS: Calculated for $C_{21}H_{26}N_4O_2 \cdot HCl$: 62.60% C; 6.75% H; 13.91% N. Found: 62.52% C; 6.71% H; 13.84% N.

EXAMPLE 16

1-(Propyl-4-pyridinylamino)-1H-indol-5-yl heptylcarbamate

To 1-(propyl-4-pyridinylamino)-1H-indol-5-ol (2.5 g) in 50 ml tetrahydrofuran was added 1,1'-carbonyldiimidazole (1.83 g) portionwise, and the reaction was allowed to proceed for 24 hours. To this mixture was added glacial acetic acid (2.15 ml) followed by a solution of heptylamine (1.45 ml) in tetrahydrofuran which had been treated with 0.56 ml of acetic acid. The reaction mixture was then stirred for 21 hours. The mixture was diluted with water, basified with sodium bicarbonate, and extracted with ethyl acetate. The organic layer was washed with water and dried (sat. NaCl, anhy. MgSO$_4$). After filtration, the solvent was evaporated to yield an oil (4.6 g), which was eluted with 5% methanol/dichloromethane on a silica gel column via HPLC. The desired fractions were concentrated to yield an oil (4.5 g), which was eluted with 5% methanol/dichloromethane on a silica gel column via HPLC. The desired fractions were concentrated to yield an oil (2.8 g). This material was dissolved in 50 ml of pentane/ether (1:1) and the solution was concentrated to 15 ml, whereupon crystals precipitated out of the solution. These were collected to yield a solid (1.0 g), m.p. 83°–85° C.

ANALYSIS: Calculated for $C_{24}H_{32}N_4O_2$: 70.56% C; 7.90% H; 13.72% N. Found: 70.33% C; 7.69% H; 13.63% N.

EXAMPLE 17

1-(Propyl-4-pyridinylamino)-1H-indol-5-yl cyclohexylcarbamate hydrochloride

Cyclohexyl isocyanate (1.7 g) was added to a solution of 1-(propyl-4-pyridinylamino)-1H-indol-5-ol (3.3 g) in 75 mL tetrahydrofuran containing potassium carbonate (milled, 2 g). After stirring twenty hours at ambient temperature, the mixture was filtered and the filtrate was concentrated. The residue was eluted through silica with ethyl acetate via flash column chromatography to yield 5 g of the product as a solid, m.p. 167°–169°. This solid was again eluted through silica with ethyl acetate via HPLC to yield 3.8 g of the product as a solid, m.p. 167°–170° C. The product was converted to the hydrochloride salt in methanol/ether to yield 3.9 g of powder, m.p. 219°–220° C. (dec.).

ANALYSIS: Calculated for $C_{23}H_{28}N_4O_2 \cdot HCl$: 64.40% C; 6.81% H; 13.06% N. Found: 64.07% C; 6.77% H; 12.92% N.

EXAMPLE 18

1-(Propyl-4-pyridinylamino)-1H-indol-5-yl phenylmethylcarbamate

Benzyl isocyanate (2 g) was added to a solution of 1-(propyl-4-pyridinylamino)-1H-indol-5-ol (3.3 g) in 75 mL tetrahydrofuran containing potassium carbonate (milled, 3 g). After stirring twenty hours at ambient temperature, the mixture was filtered and the filtrate was concentrated. The residue was eluted through silica with ethyl acetate via flash column chromatography to yield 5 g of the product as a solid, m.p. 156°–158° C. The product was recrystallized from acetonitrile to yield 3.8 g of crystals, m.p. 162°–164° C.

ANALYSIS: Calculated for $C_{24}H_{24}N_4O_2$: 71.98% C; 6.04% H; 13.99% N. Found: 71.99% C; 6.13% H; 14.03% N.

EXAMPLE 19

1-(Propyl-4-pyridinylamino)-1H-indol-5-yl 4-chlorophenylmethylcarbamate

To a solution of 1-(propyl-4-pyridinylamino)-1H-indol-5-ol (2.5 g) in 60 ml of tetrahydrofuran was added 1,1'-carbonyldiimidazole (1.83 g) and this mixture was stirred for 24 hours. Then 4.5 ml of glacial acetic acid was added to the reaction mixture followed by 4-chlorophenylmethylamine (1.5 g) in 10 ml of tetrahydrofuran. This mixture was then stirred for 24 hours, quenched with water and basified with saturated sodium carbonate solution and extracted with ethyl acetate. The organic layer was washed with water and dried (sat. NaCl, anhy. MgSO$_4$). After filtration, the solvent was evaporated to yield an oil (3.9 g), which was eluted with 5% methanol in dichloromethane on a silica gel column via HPLC. The desired fractions were concentrated to yield a solid (3.05 g), m.p. 149°-151° C.

ANALYSIS: Calculated for: 66.29% C; 5.33% H; 12.88% N. Found: 66.22% C; 5.37% H; 12.81% N.

EXAMPLE 20

1-(Propyl-4-pyridinylamino)-1H-indol-5-yl 2-phenylethylcarbamate hydrochloride

2-Phenylethyl isocyanate (2.1 g) was added to a solution of 1-(propyl-4-pyridinylamino)-1H-indol-5-ol (3 g) in 75 mL tetrahydrofuran containing potassium carbonate (milled, 3.5 g). After stirring three hours at ambient temperature, the mixture was filtered and the filtrate was concentrated. The residue was eluted through silica with ethyl acetate via flash column chromatography to yield 4.7 g of the product as a solid. The product was converted to the hydrochloride salt in methanol/ether to yield 2.9 g of crystals, m.p. 144°-146° C. (dec.).

ANALYSIS: Calculated for $C_{25}H_{26}N_4O_2 \cdot HCl$: 66.58% C; 6.04% H; 12.43% N. Found: 66.60% C; 5.94% H; 12.38% N.

EXAMPLE 21

(S)-(−)-1-(Propyl-4-pyridinylamino)-1H-indol-5-yl 1-phenylethylcarbamate

To 1-(propyl-4-pyridinylamino)-1H-indol-5-ol (1.75 g) in 30 ml of tetrahydrofuran was added potassium carbonate (milled, 0.912 g) followed by (S)-(−)-1-methylbenzyl isocyanate (0.97 g), and the reaction was allowed to proceed for one hour. The reaction mixture was filtered and the filtrate concentrated to yield an oil (3.9 g) which was eluted with 5% methanol in dichloromethane (DCM) on a silica gel column via HPLC. The desired fractions were concentrated to yield a solid 2.6 g, m.p. 78°-80° C.

ANALYSIS: Calculated for $C_{25}H_{26}N_7O_2$: 72.44% C; 6.32% H; 13.52% N. Found: 72.17% C; 6.34% H; 13.49% N.

EXAMPLE 22

1-(Propyl-4-pyridinylamino)-1H-indol-5-yl dimethyl carbamate

To a solution of 1-(propyl-4-pyridinylamino)-1H-indol-5-ol (2.5 g) in 60 ml of tetrahydrofuran was added 1,1'-carbonyldiimidazole (1.83 g) and this mixture was stirred for 24 hours. Then 4.5 ml of glacial acetic acid was added to the reaction mixture followed by dimethylamine (40 wt % in water, 1.44 ml) in 10 ml of tetrahydrofuran. This mixture was then stirred for 24 hours, quenched with water and basified with saturated sodium carbonate solution and extracted with ethyl acetate. The organic layer was washed with water and dried (sat. NaCl., anhy. MgSO4). After filtration, the solvent was evaporated to yield an oil (3.5 g), which was eluted with 5% methanol in dichloromethane on a silica gel column via HPLC. The desired fractions were concentrated to yield a solid (2.5 g), m.p. 134°-136° C.

ANALYSIS: Calculated for: 67.43% C; 6.55% H; 16.56% N. Found: 67.63% C; 6.58% H; 16.58% N.

EXAMPLE 23

1-(Propyl-4-pyridinylamino)-1H-indol-5-yl piperidinylcarbamate

To a solution of 1-(propyl-4-pyridinylamino)-1H-indol-5-ol (2.5 g) in 60 ml of tetrahydrofuran was added 1,1'-carbonyldiimidazole (1.83 g) and this mixture was stirred for 24 hours. Then 4.5 ml of glacial acetic acid was added to the reaction mixture followed by piperidine (0.95 g) in 10 ml of tetrahydrofuran. This mixture was then stirred for 24 hours, quenched with water and basified with saturated sodium carbonate solution and extracted with ethyl acetate. The organic layer was washed with water and dried (sat. NaCl, anhy. MgSO4). After filtration, the solvent was evaporated to yield an oil (4.6 g), which was eluted with 5% methanol in dichloromethane on a silica gel column via HPLC. The desired fractions were concentrated to yield an oil (3.65 g).

ANALYSIS: Calculated for $C_{22}H_{26}N_4O_2$: 69.81% C; 6.92% H; 14.80% N. Found: 69.45% C; 6.94% H; 14.68% N.

EXAMPLE 24

1-(Propyl-4-pyridinylamino)-1H-indol-5-yl 1,2,3,4-tetrahydro-2-isoquinolinylcarbamate To a solution of 1-(propyl-4-pyridinylamino)-1H-indol-5-ol (2.5 g) in 40 ml of tetrahydrofuran was added 1,1'-carbonyldiimidazole (1.83 g) and this mixture was stirred for 24 hours. Then 3.5 ml of glacial acetic acid was added to the reaction mixture. Then 1,2,3,4-tetrahydroisoquinoline (1.49 g) in 10 ml of tetrahydrofuran which had been acidified with 0.60 ml of glacial acetic acid was added to the reaction mixture dropwise. This was stirred for 24 hours and then the reaction mixture was quenched with water, basified with saturated sodium carbonate solution and extracted with ethyl acetate. The organic layer was washed with water and dried (sat. NaCl, anhy. MgSO4). After filtration, the solvent was evaporated to yield an oil (5.6 g) which was eluted with 5% methanol/dichloromethane on a silica gel column via HPLC. The desired fractions were concentrated to yield an oil (4.2 g). This material was dissolved in pentane/ether (1:1), whereupon a solid precipitated out of the solution. This material was collected to yield a solid, 2.6 g, m.p. 141°-143° C.

ANALYSIS: Calculated for $C_{26}H_{26}N_4O_2$: 73.21% C; 6.15% H; 13.14% N. Found: 73.12% C; 6.22% H; 12.95% N.

EXAMPLE 25

1-(3-Fluoro-4-pyridinylamino)-5-phenylmethoxy-1H-indole

To 250 ml 1-methyl-2-pyrrolidinone was added 5-phenylmethoxy-1H-indol-1-amine (27.3 g), and the mixture was heated to 80° C. Then, 4-chloro-3-fluoropyridine hydrochloride (22 g) was added, and the mixture was heated at 80° C. for two hours. After cooling, the mixture was poured into 1 liter of ice-water, stirred for five minutes, and adjusted to pH 9 with milled $K_2CO_3$. The product was extracted with ethyl acetate (3×). The organic layer was washed with water (2×) and dried (saturated NaCl, anhydrous MgSO4). After filtration, the filtrate was concentrated to give an oil, 46 g of which was eluted on a silica gel column with ethyl acetate/dichloromethane (1:1) via HPLC. The desired fractions were combined and concentrated to give an oil, which solidified on cooling, 32.2 g, m.p. 140° C. A sample of this material was recrystallized from ether, m.p. 157°-159° C.

ANALYSIS: Calculated for $C_{20}H_{16}FN_3O$: 72.06% C; 4.84% H; 12.60% N. Found: 71.98% C; 4.90% H; 12.51% N.

EXAMPLE 26

1-[(3-Fluoro-4-pyridinyl)propylamino]-5-phenylmethoxy-1H-indole hydrochloride

To 100 ml of dry DMF (dimethylformamide) was added 1-(3-fluoro-4pyridinylamino)-5-phenylmethoxy-1H-indole (20.0 g), and the solution was cooled to 0° C. To this was added potassium t-butoxide (6.7 g), and the mixture was stirred at 0° C. for ten minutes, and thereafter a solution of n-propylbromide (5.5 ml) in 10 ml dry DMF was added. After stirring at 0° C. for thirty minutes and then at ambient temperature for two hours, the mixture was poured into 500 ml cold water, stirred for five minutes and extracted with ethyl acetate (3×). The organic layer was washed successively with water (2×) and saturated sodium chloride solution, and then dried over anhydrous magnesium sulfate. After filtration, the filtrate was concentrated to give an oil, 23 g, which was eluted on a silica gel column with ethyl acetate/dichloromethane (1:2) via HPLC. The desired fractions were combined and concentrated to give an oil, 19.3 g. A 2.0 g sample of this oil was dissolved in 50 ml methanol, and the solution was acidified to pH 1 with ethereal HCl and diluted with 200 ml ether. The resultant precipitate was collected and dried to give 2.1 g, m.p. 200° C. (dec.).

ANALYSIS: Calculated for $C_{23}H_{22}FN_3O \cdot HCl$: 67.06% C; 5.63% H; 10.20% N. Found: 66.74% C; 5.55% H; 10.05% N.

EXAMPLE 27

1-(3-Fluoro-4-pyridinylamino)-1H-indol-5-ol

In a 500 ml Parr hydrogenation bottle, 10% Pd/C (1.0 g) was suspended in 50 ml ethanol, and to this was added a solution of 1-(3-fluoro-4-pyridinylamino)-5-phenylmethoxy-1H-indole (5.0 g) in 200 ml ethanol. The mixture was shaken at 50° C. under 50 psi hydrogen gas for two hours. After cooling, the mixture was filtered, and the filtrate was concentrated to give an oil (5.0 g) which was eluted on a silica gel column with ethyl acetate/dichloromethane (1:1) via HPLC. The desired fractions were combined and concentrated to give a crystalline solid, 3.5 g, m.p. 70°-73° C.

ANALYSIS: Calculated for $C_{13}H_{10}FN_3O$: 64.19% C; 4.14% H; 17.28% N. Found: 64.06% C; 4.30% H; 16.93% N.

EXAMPLE 28

1-[(3-Fluoro-4-pyridinyl)propylamino]-1H-indol-5-ol hydrochloride

In a 500 ml Parr hydrogenation bottle, 10% Pd/C (1.5 g) was suspended in 50 ml ethanol, and to this was added a solution of 1-[(3-fluoro-4-pyridinyl)propylamino]-5-phenylmethoxy-1H-indole (15.0 g) in 200 ml ethanol. The mixture was shaken under 50 psi hydrogen gas for three hours at 50° C. Upon cooling, the mixture was filtered, and the filtrate was concentrated to give a solid, 11.4 g. This material was eluted on a silica gel column with ethyl acetate/dichloromethane (1:3) via HPLC, and the desired fractions were concentrated to give a solid, 8.5 g, m.p. 90°-95° C. A 2.0 g sample of this material was dissolved in 50 ml methanol, the pH was adjusted to 1 with ethereal HCl, and the solution was diluted with 200 ml ether. The resultant precipitate was collected and dried to give 2.1 g of the product, m.p. 218° C. (dec.).

ANALYSIS: Calculated for $C_{16}H_{16}FN_3O \cdot HCl$: 59.72% C; 5.33% H; 13.06% N. Found: 59.30% C; 5.36% H; 12.62% N.

EXAMPLE 29

1-[(3-Fluoro-4-pyridinyl)propylamino]-1H-indol-5-yl methylcarbamate

To a solution of 1-[(3-fluoro-4-pyridinyl)propylamino]-1H-indol-5-ol (2.5 g) in 50 ml THF was added potassium carbonate (1.2 g), followed by methyl isocyanate (0.53 ml). After stirring at ambient temperature for three hours, the mixture was filtered, and the filtrate was concentrated to give a solid, 3.0 g, m.p. 165°-166° C.. This material was eluted on a silica gel column with ethyl acetate/dichloromethane (1:1) via HPLC. The desired fractions were combined and concentrated to give a solid, 2.7 g, m.p. 177°-178° C.

ANALYSIS: Calculated for $C_{18}H_{19}FN_4O_2$: 63.14% C; 5.59% H; 16.37% N. Found: 63.27% C; 5.68% H; 16.23% N.

EXAMPLE 30

1-[(3-Fluoro-4-pyridinyl)propylamino]-1H-indol-5-yl butylcarbamate hydrochloride To a solution of 1-[(3-fluoro-4-pyridinyl)propylamino]-1H-indol-5-ol (2.2 g) in 50 ml tetrahydrofuran was added milled $K_2CO_3$ (1.1 g), followed by butyl isocyanate (0.9 ml). After stirring at ambient temperature for four hours, the mixture was filtered, and the filtrate was concentrated to give an oil, 5 g. This oil was eluted on a silica gel column with ethyl acetate/dichloromethane (1:4) via HPLC. The desired fractions were combined and concentrated to give an oil, which solidified on standing, 2.7 g, m.p. 95°-98° C.

This solid was dissolved in ether, the pH was adjusted to 1 with ethereal HCl, and the resultant precipitate was collected and dried to give 2.9 g of a solid, m.p. 140° C. (dec.). This material was recrystallized from ethyl acetate/ether (1:10) to give the product as crystals, 2.4 g, m.p. 142° C. (dec.).

ANALYSIS: Calculated for $C_{21}H_{25}FN_4O_2 \cdot HCl$: 59.92% C; 6.23% H; 13.31% N. Found: 60.31% C; 6.26% H; 13.31% N.

EXAMPLE 31

1-[(3-Fluoro-4-pyridinyl)propylamino]-1H-indol-5-yl heptylcarbamate hydrochloride To a solution of 1-[(3-fluoro-4-pyridinyl)propylamino]-1H-indol-5-ol (2.2 g) in 65 ml tetrahydrofuran was added 1,1'-carbonyldiimidazole (1.5 g), and the mixture was stirred at ambient temperature for four hours. The mixture was cooled with an ice bath, and thereafter glacial acetic acid (2.0 ml) was added, followed by a solution of heptylamine (2 ml) and acetic acid in tetrahydrofuran (20 ml).

After stirring at ambient temperature for twenty hours, the mixture was poured into 200 ml water, the pH adjusted to 8 with $NaHCO_3$ solution, and the product was extracted with ethyl acetate. The organic layer was washed successively with water and saturated NaCl solution, and dried over anhydrous $MgSO_4$. After filtration, the filtrate was concentrated to give an oil, 4.2 g, which was eluted on a silica gel column with ethyl acetate/dichloromethane (1:3) via HPLC. The desired fractions were combined and concentrated to give an oil, 2.6 g. This oil was dissolved in ether, the pH was adjusted to 1 with ethereal HCl, and the resultant precipitate was collected and dried to give 2.5 g of solid, m.p. 140° C. (dec.). This material was recrystallized from ethyl acetate/ether (1:4) to give crystals, 2.3 g, m.p., 246° C. (dec.).

ANALYSIS: Calculated for $C_{24}H_{31}FN_4O_2.HCl$: 62.26% C; 6.97% H; 12.10% N. Found: 62.62% C; 7.08% H; 12.06% N.

EXAMPLE 32

3-Methyl-5-(phenylmethoxy)-1H-indol-1-amine p-Benzyloxyphenylhydrazine hydrochloride was prepared by the method of Mentzer, et al., [C.A. 48:33412]. Thus, p-benzyloxyaniline hydrochloride (72.6 g) was diazotized with conc. HCl (174 ml) and sodium nitrite (23.2 g) in water (40 ml) at 0° C. A solution of stannous chloride (169.3 g) in conc. HCl (435 ml) was added rapidly and the reaction mixture stirred for two hours. The solid product was filtered and washed with absolute ethanol, then partially dissolved in boiling methanol/ethanol (1:1) and filtered hot, yielding 52.5 g of p-benzyloxyphenylhydrazine hydrochloride.

The conversion of the above compound to 3-methyl-5-benzyloxyindole was conducted according to the method of Keglevic, et al. [C.A. 56:4710 h]. Thus, the above hydrazine hydrochloride (34.0 g) was dissolved in 25% aqueous HOAc (1.4 L) at 80° C. Propionaldehyde diethyl acetal (22.1 ml) was then added and the reaction mixture stirred for 0.75 hour. Upon cooling to room temperature, ether was added to the reaction mixture and the layers were separated. The aqueous phase was extracted with ether (2×). The combined organics were washed with 5% aqueous NaOH until the aqueous extract was basic to litmus. The organic phase was then washed with brine and dried ($K_2CO_3$). Filtration and concentration afforded 29.0 g of 3-methyl-5-benzyloxyindole. 3-Methyl-5-(phenylmethoxy)-1H-indol-1-amine was prepared using the procedure of Somei, et al., [Tetrahedron Lett. No. 5, pp. 461–462, 1974]. Thus, to a solution of the above product (17.3 g) in dry DMF (260 ml) maintained at 0° C. was added milled potassium hydroxide (20.5 g) under nitrogen. Hydroxylamine-O-sulfonic acid (10.7 g) was added portionwise (10% wt.) every ten minutes. After stirring for 1 hour at room temperature, water and ethyl acetate were added to the reaction mixture. The layers were separated and the aqueous phase was extracted with ethyl acetate (3×). The combined organic layers were washed with brine and dried ($K_2CO_3$). Filtration and concentration gave the crude product.

Purification via preparative HPLC (silica gel, DCM) afforded 6.0 g of the desired product as a solid which was recrystallized from ether, m.p. 104°-106° C.

ANALYSIS: Calculated for $C_{16}H_{16}N_2O$: 76.16% C; 6.39% H; 11.10% N. Found: 75.86% C; 6.37% H; 10.87% N.

EXAMPLE 33

3-Methyl-5-(phenylmethoxy)-1-(4-pyridinylamino)-1H-indole

To a solution consisting of 3-methyl-5-(phenylmethoxy)-1H-indol-1-amine (6.31 g) and 1-methyl-2-pyrrolidinone (109 ml) was added 4-chloropyridine hydrochloride (3.94 g). The resulting mixture was heated at 80° C. for 4–5 hours. Another batch of reaction was also carried out with the amine (2.94 g) and 4-chloropyridine hydrochloride (1.84 g) in nmp (50 ml) at 80° C. for 4 hours. The above reaction mixtures were poured together into dilute aqueous sodium bicarbonate and extracted with EtOAc (4×) and ether (1×). The combined organic layers were washed with water and brine followed by drying ($K_2CO_3$). Filtration, concentration and purification via flash column chromatography (silica gel, 2% $Et_3N$/ether/0–5% MeOH) afforded 7.55 g of the desired product. Recrystallization from EtOAc gave a solid, m.p. 167.5°-169.5° C.

ANALYSIS: Calculated for $C_{21}H_{19}N_3O$: 76.57% C; 5.81% H; 12.76% N. Found: 76.73% C; 6.05% H; 12.76% N.

EXAMPLE 34

3-Methyl-1-(4-pyridinylamino)-1H-indol-5-ol

3-Methyl-5-phenylmethoxy-1-(4-pyridinylamino)-1H-indole (2.20 g) was subjected to hydrogenolysis in absolute ethanol (80 ml) with 10% Pd-C (0.26 g) at 50 psig hydrogen at 50° C. for 2 hours. The catalyst was removed by filtration through a pad of celite and the solids washed with methanol. Concentration and recrystallization from methanol afforded 0.50 g of highly crystalline product, m.p. 239°-241° C. (dec.).

ANALYSIS: Calculated for $C_{14}H_{13}N_3O$: 70.28% C; 5.48% H; 17.56% N. Found: 69.95% C; 5.46% H; 17.41% N.

EXAMPLE 35

3-Methyl-5-(phenylmethoxy)-1-(propyl-4-pyridinylamino)-1H-indole hemifumarate

To a solution consisting of 3-methyl-5-(phenylmethoxy)-1-(4-pyridinylamino)-1H-indole (7.78 g) and dimethylformamide (150 ml) maintained at 0° C. under nitrogen with stirring, was added sodium hydride (0.64 g, 97% purity). The resulting mixture was stirred at 0° C. for an additional 15 minutes at which time propyl bromide (2.25 ml) was added dropwise and the ice bath was removed. Stirring was continued at room temperature for 2–3 hours until complete reaction was observed by TLC (silica gel, ether). The reaction mixture was poured into water and the product extracted with EtOAc (3x) and ether (1x). The combined organic layers were washed successively with water (2x) and brine (2x), dried ($K_2CO_3$) and decolorized with activated carbon. Filtration and concentration gave the desired product (7.65 g) as an oil. The hemifumarate was prepared with 1.0 eq. fumaric acid in abs. ethanol. A highly crystalline solid resulted, m.p. 165°-167° C.

ANALYSIS: Calculated for $C_{24}H_{25}N_3O.0.5C_4H_4O_4$: 72.70% C; 6.35% H; 9.78% N. Found: 72.66% C; 6.55% H; 9.73% N.

EXAMPLE 36

3-Methyl-1-(propyl-4-pyridinylamino)-1H-indol-5-ol hemioxalate

The benzyl group of 3-methyl-5-(phenylmethoxy)-1-(propyl-4-pyridinylamino)-1H-indole (7.80 g) was cleaved in a Parr hydrogenation apparatus in abs. EtOH (275 ml) over 10% Pd-C (0.80 g) at 50 psig and 50° C. for 2–3 hours. The catalyst was removed by filtration through a pad of celite and the solids washed with methanol. The combined filtrate was concentrated and the product purified via flash column chromatography (silica gel, 2% $Et_3N$/ether) affording 5.80 g of the product as an oil. Dissolving in absolute ethanol followed by addition of 1.0 eq of anhydrous oxalic acid (in abs. EtOH) resulted in formation of a solid, the hemioxalate, m.p. 235°–237° C.

ANALYSIS: Calculated for $C_{17}H_{19}N_3O \cdot 0.5C_2H_2O_4$: 66.23% C; 6.19% H; 12.88% N. Found: 65.91% C; 6.33% H; 12.58% N.

EXAMPLE 37

3-Methyl-1-(propyl-4-pyridinylamino)-1H-indol-5-yl methylcarbamate

To a stirred solution consisting of 3-methyl-1-(propyl-4-pyridinylamino)-1H-indol-5-ol (2.06 g) and tetrahydrofuran (49 ml) was added milled $K_2CO_3$ (1.06 g) followed by dropwise addition of methyl isocyanate (0.48 ml) at room temperature under nitrogen. Stirring was continued for 2.3 hours at which time the reaction mixture was filtered through a pad of celite and the solids washed with EtOAc. Concentration afforded the crude product. Purification via flash column chromatography (silica gel, 2% $Et_3N$/EtOAc) afforded 2.30 g of the desired carbamate as an oil. The product was crystallized from ether, m.p. 147°–149° C.

ANALYSIS: Calculated for $C_{19}H_{22}N_4O_2$: 67.44% C; 6.55% H; 16.56% N. Found: 67.49% C; 6.68% H; 16.53% N.

EXAMPLE 38

3-Methyl-1-(propyl-4-pyridinylamino)-1H-indol-5-yl butylcarbamate

To a stirred solution consisting of 3-methyl-1-(propyl-4-pyridinylamino)-1H-indol-5-ol (2.11 g) and tetrahydrofuran (50 ml) was added milled $K_2CO_3$ (1.09 g), followed by dropwise addition of butyl isocyanate (0.93 ml) at room temperature under nitrogen. Stirring was continued for 2.0 hours at which time the reaction mixture was filtered through a pad of celite and the solids washed with EtOAc. Concentration afforded the crude product. Purification via flash column chromatography (silica gel, 2% $Et_3N$/EtOAc) afforded 2.65 g of the desired carbamate as an oil. This oil was dissolved in a small amount of EtOAc and diluted with ether, whereupon the product crystallized as a white powder, m.p. 120°–122° C.

ANALYSIS: Calculated for $C_{22}H_{28}N_4O_2$: 69.45% C; 7.42% H; 14.72% N. Found: 69.67% C; 7.44% H; 14.68% N.

EXAMPLE 39

3-Methyl-1-(propyl-4-pyridinylamino)-1H-indol-5-yl heptylcarbamate

To a solution consisting of 3-methyl-1-(propyl-4-pyridinylamino)-1H-indol-5-ol (2.23 g) and tetrahydrofuran (53 ml) was added 1,1'-carbonyldiimidazole (2.57 g) at room temperature with stirring under nitrogen. Stirring was continued for 96 hours, at which time acetic acid (1.54 ml) was added. To the resulting reaction mixture was added a solution consisting of heptyl amine (1.76 ml), acetic acid (0.71 ml) and THF (5 ml). After stirring for 24 hours, an additional solution of heptyl amine (1.17 ml), acetic acid (0.48 ml) and THF (5 ml) was added and stirring continued for 3 hours. The reaction mixture was poured into a dilute aqueous sodium bicarbonate solution and the product extracted with ether (3x). The combined organic layer was washed with brine and dried ($MgSO_4$). Filtration, concentration and purification via flash column chromatography (silica gel, 2% $Et_3N$/ether) afforded 1.60 g of the desired carbamate after recrystallization from ether/pentane, m.p. 102°–104° C.

ANALYSIS: Calculated for $C_{25}H_{34}N_4O_2$: 71.06% C; 8.11% H; 13.26% N. Found: 71.10% C; 8.08% H; 13.25% N.

EXAMPLE 40

3-Methyl-1-(propyl-4-pyridinylamino)-1H-indol-5-yl phenylmethylcarbamate

To a solution consisting of 3-methyl-1-(propyl-4-pyridinylamino)-1H-indol-5-ol (1.80 g) and tetrahydrofuran (43 ml) were added with stirring at room temperature milled potassium carbonate (0.93 g) and benzyl isocyanate (0.87 ml). Stirring was continued under nitrogen for 16 hours. The mixture was filtered through a pad of celite and the solids washed with ethyl acetate. Concentration followed by purification via flash column chromatography (silica gel, 2% $Et_3N$/EtOAc) afforded 2.28 g of the desired carbamate. Recrystallization from ether gave a highly crystalline solid, m.p. 149°–151° C.

ANALYSIS: Calculated for $C_{25}H_{26}N_4O_2$: 72.44% C; 6.32% H; 13.52% N. Found: 72.39% C; 6.73% H; 13.92% N.

EXAMPLE 41

3-Methyl-1-(propyl-4-pyridinylamino)-1H-indol-5-yl, 1,2,3,4-tetrahydro-2-isoquinolylincarbamate To a solution consisting of 3-methyl-1-(propyl-4-pyridinylamino)-1H-indol-5-ol (1.67 g) and tetrahydrofuran (40 ml) was added 1,1'-carbonyldiimidazole (1.92 g) at room temperature with stirring under nitrogen. Stirring was continued for 48 hours, at which time acetic acid (1.6 ml) was added. To the resulting reaction mixture was added a solution consisting of 1,2,3,4-tetrahydroisoquinoline (1.6 ml), acetic acid (0.76 ml) and THF (10 ml). After stirring for 16 hours, the reaction mixture was poured into a dilute aqueous sodium bicarbonate solution and the product extracted with ether (3x). The combined organic layer was washed with brine and dried ($MgSO_4$). Filtration, concentration and purification via flash column chromatography (silica gel, 2% $Et_3N$/ether) gave 2.41 g of the desired carbamate as a foam. The compound formed a white powder in ether/pentane, m.p. 160°–162° C.

ANALYSIS: Calculated for $C_{27}H_{28}N_4O_2$: 73.61% C; 6.41% H; 12.72% N. Found: 73.57% C; 6.38% H; 12.61% N.

EXAMPLE 42

1-[(3-Fluoro-4-pyridinyl)amino]-3-methyl-5-(phenylmethoxy)-1H-indole

To a solution consisting of 3-methyl-5-(phenylmethoxy)-1H-indol-1-amine (4.81 g) and 1-methyl-2-pyrrolidinone (83 ml) was added 4-chloro-3-fluoro pyridine hydrochloride (3.20 g). The resulting mixture was heated at 80° C. for 2 hours. Upon cooling to room temperature, dilute aqueous sodium bicarbonate and ethyl acetate were added to the reaction mixture. The layers were separated and the aqueous phase was extracted with EtOAc (3x). The combined organic layers were washed successively with water (2x) and brine (1x), and thereafter dried ($MgSO_4$). Filtration and concentration gave the crude product. Purification via flash column chromatography (silica gel, 50% ethyl acetate/- dichloromethane) afforded 4.0 g of the desired product as a solid, m.p. 210°-213° C.

EXAMPLE 43

1-[(3-Fluoro-4-pyridinyl)propylamino]-3-methyl-5-(phenylmethoxy)-1H-indole

To a solution consisting of 1-[(3-fluoro-4-pyridinyl)amino]-3-methyl-5-(phenylmethoxy)-1H-indole (3.76 g) and dimethylformamide (108 ml), cooled to 0° C. under nitrogen with stirring, was added sodium hydride (0.29 g). The resulting mixture was stirred at 0° C. for an additional 15 minutes, at which time 1-bromopropane (1.03 ml) was added dropwise and the ice bath removed. Stirring was continued at room temperature overnight, at which time the reaction appeared complete by TLC (silica gel, 50% ether/hexane). The reaction mixture was poured into water and the product extracted with EtOAc (3x). The combined organic layers were washed with brine and dried (MgSO$_4$). Filtration and concentration gave the crude product as an oil. Purification via preparative HPLC (silica gel, 30% EtOAc/hexane) afforded 2.80 g of the desired product as a solid which was recrystallized from ether, m.p. 94°-96° C.

ANALYSIS: Calculated for C$_{24}$H$_{24}$FN$_3$O: 74.01% C; 6.21% H; 10.79% N. Found: 73.58% C; 6.09% H; 10.56% N.

EXAMPLE 44

1-[(3-Fluoro-4-pyridinyl)propylamino]-3-methyl-1H-indol-5-ol

The benzyl group of 1-[(3-fluoro-4-pyridinyl)propylamino]-3-methyl-5-(phenylmethoxy)-1H-indole (15.82 g) was cleaved in a Parr hydrogenation apparatus in absolute ethanol (200 ml) over 10% Pd-C (1.58 g) at 50 psig and 50° C. for 7.5 hours. The catalyst was removed by filtration through a pad of celite and the solids washed with absolute ethanol. The combined filtrate was concentrated and the product purified via preparative HPLC (silica gel, 3:1 dichloromethane/EtOAc) affording 5.0 g of the desired product as an oil. Addition of EtOAc solidified the product which was recrystallized from EtOAc to give a solid, m.p. 157°-160° C.

ANALYSIS: Calculated for C$_{17}$H$_{18}$FN$_3$O: 68.21% C; 6.06% H; 14.04% N. Found: 67.81% C; 6.09% H; 13.73% N.

EXAMPLE 45

1-[(3-Fluoro-4-pyridinyl)propylamino]-3-methyl-1H-indol-5-yl methylcarbamate

To a solution consisting of 1-[(3-fluoro-4-pyridinyl)propylamino]-3-methyl-1H-indol-5-ol (2.10 g) and tetrahydrofuran (47 ml) was added milled K$_2$CO$_3$ (1.02 g) followed by dropwise addition of methyl isocyanate (0.46 ml) at room temperature under nitrogen. Stirring was continued for 15 hours, at which time the reaction mixture was filtered through a pad of celite and the solids washed with EtOAc. Concentration afforded the crude product. Purification via flash column chromatography (silica gel, 50% EtOAc/dichloromethane) afforded 2.35 g of the desired carbamate as a solid. The product was recrystallized from ether, m.p. 163°-164° C.

ANALYSIS: Calculated for C$_{19}$H$_{21}$FN$_4$O$_2$: 64.03% C; 5.94% H; 15.72% N. Found: 63.84% C; 6.10% H; 15.55% N.

EXAMPLE 46

1-[(3-Fluoro-4-pyridinyl)propylamino]-3-methyl-1H-indol-5-yl butylcarbamate

To a stirred solution consisting of 1-[(3-fluoro-4-pyridinyl)propylamino]-3-methyl-1H-indol-5-ol (2.10 g) and tetrahydrofuran (47 ml) was added milled K$_2$CO$_3$ (1.02 g) followed by dropwise addition of butyl isocyanate (0.87 ml) at room temperature under nitrogen. Stirring was continued for 15 hours, at which time the reaction mixture was filtered through a pad of celite and the solids washed with EtOAc. Concentration afforded the crude product. Purification via flash column chromatography (silica gel, ether) afforded 2.3 g of the desired product as an oil. The product was crystallized from ether/pentane, m.p. 83°-84° C.

ANALYSIS: Calculated for C$_{22}$H$_{27}$FN$_4$O$_2$: 66.31% C; 6.83% H; 14.06% N. Found: 65.99% C; 6.83% H; 13.88% N.

EXAMPLE 47

1-[(3-Fluoro-4-pyridinyl)propylamino]-3-methyl-1H-indol-5-yl heptylcarbamate

To a solution consisting of 1-[(3-fluoro-4-pyridinyl)propylamino]-3-methyl-1H-indol-5-ol (2.54 g) and anhydrous tetrahydrofuran (57 ml) was added carbonyl diimidazole (2.75 g) under nitrogen with stirring. The resulting reaction mixture was stirred at room temperature for two days, at which time acetic acid (1.65 ml) was added followed by a solution of heptylamine (1.89 ml) in tetrahydrofuran (5 ml) and acetic acid (0.76 ml). After stirring for 24 hours, an additional equivalent of heptylamine (1.26 ml) in tetrahydrofuran (5 ml) and acetic acid (0.52 ml) was added. After an additional 24 hours the reaction was complete and the reaction mixture was poured into NaHCO$_3$ (aq.) and ether. The layers were separated and the aqueous phase was extracted with ether (3x). The combined organic layers were washed successively with NaHCO$_3$ (aq.) and brine. Drying (Na$_2$SO$_4$), filtration and concentration gave a crude product. Purification via flash column chromatography (silica gel, 30% EtOAc/hexane) afforded 3.38 g of the desired product as an oil. Addition of ether and pentane solidified the product. The solid was filtered and washed with pentane, m.p. 90°-93° C.

ANALYSIS: Calculated for C$_{25}$H$_{33}$FN$_4$O$_2$: 68.16% C; 7.55% H; 12.72% N. Found: 67.87% C; 7.35% H; 12.60% N.

EXAMPLE 48

1-[(3-Fluoro-4-pyridinyl)propylamino]-3-methyl-1H-indol-5-yl phenylmethylcarbamate To a stirred solution of 1-[(3-fluoro-4-pyridinyl)propylamino]-3-methyl-1H-indol-5-ol (2.66 g) in tetrahydrofuran (59 ml) was added milled potassium carbonate (1.29 g) followed by dropwise addition of benzyl isocyanate (1.21 ml) at room temperature under nitrogen. Stirring was continued for 17.0 hours at which time the reaction mixture was filtered through a pad of celite and the solids washed with ethyl acetate. Concentration afforded a crude product. Purification via flash column chromatography (silica gel, ether) afforded 3.34 g of the desired carbamate as a foam. This foam was dissolved in ether and the product crystallized as a solid. The solid was recrystallized from ether, m.p. 143°-144° C.

ANALYSIS: Calculated for $C_{25}H_{25}FN_4O_2$: 69.42% C; 5.83% H; 12.96% N. Found: 69.44% C; 5.83% H; 12.84% N.

EXAMPLE 49

1-[(3-Fluoro-4-pyridinyl)propylamino]-3-methyl-1H-indol-5-yl 1,2,3,4-tetrahydro-2-isoquinolinylcarbamate To a stirred solution of 1-[(3-fluoro-4-pyridinyl)propylamino]-3-methyl-1H-indol-5-ol (2.51 g) in anhydrous tetrahydrofuran (56 ml) was added 1,1'-carbonyl diimidazole (2.72 g) at room temperature under nitrogen. After 24 hours the reaction appeared complete by TLC (silica gel, 60% EtOAc/hexane) and acetic acid (1.60 ml) was added to the reaction mixture followed by the dropwise addition of a solution of 1,2,3,4-tetrahydroisoquinoline (1.58 ml) in tetrahydrofuran (5.0 ml) and acetic acid (0.75 ml). After 72 hours, the reaction was not complete by TLC (60% EtOAc/dichloromethane) and an additional equivalent of 1,2,3,4-tetrahydroisoquinoline (1.05 ml) was added as a tetrahydrofuran (5.0 ml) and acetic acid (0.51 ml) solution. After 1.5 hours the reaction appeared complete and the mixture was poured into NaHCO$_3$ (aq) and ether. The layers were separated and the aqueous phase was extracted with ether (3x). The combined organic layers were washed successively with NaHCO$_3$ (aq) and brine, and dried (Na$_2$SO$_4$). The organic phase was filtered and concentrated to give a crude product. Purification via flash column chromatography (silica gel., 30% EtOAc/dichloromethane) afforded 2.70 g of the desired product as an oil which solidified on standing. Recrystallization from ether (2x) gave a solid which was filtered and washed with ether, m.p. 157°–160° C.

ANALYSIS: Calculated for $C_{27}H_{27}FN_4O_2$: 70.72% C; 5.94% H; 12.22% N. Found: 70.93% C; 5.85% H; 12.11% N.

We claim:
1. A compound having the formula,

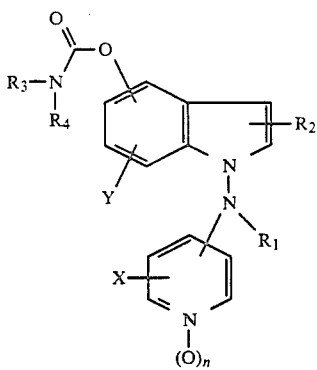

where
n is 0 or 1;
X is hydrogen, halogen, nitro, amino, trifluoromethyl, loweralkyl, or loweralkoxy;
Y is hydrogen, halogen, nitro, amino, trifluoromethyl, loweralkyl, or loweralkoxy;
R$_1$ is hydrogen, loweralkyl, arylloweralkyl, loweralkenyl, loweralkynyl, loweralkanoyl, arylloweralkanoyl, heteroarylloweralkyl or heteroarylloweralkanoyl;
R$_2$ is hydrogen, loweralkyl, formyl or cyano;
R$_3$ is hydrogen or loweralkyl;
R$_4$ is loweralkyl, arylloweralkyl, cycloalkyl, aryl or heteroaryl; or alternatively, —NR$_3$R$_4$ taken together constitutes

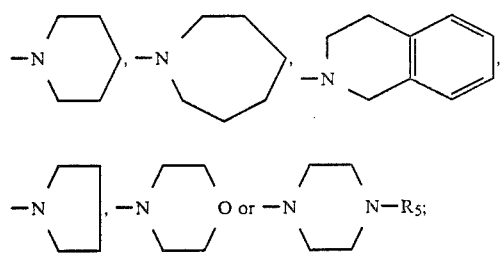

R$_5$ being hydrogen, loweralkyl, aryl, heteroaryl or heteroarylloweralkyl, the term aryl in each occurrence signifying a phenyl group substituted with 0, 1 or 2 substituents which of each being independently loweralkyl, loweralkoxy, halogen or trifluoromethyl;
the term heteroaryl in each occurrence signifying furyl, thienyl, pyrrolyl or pyridinyl; and
the term cycloalkyl in each occurrence signifying a cycloalkyl group of 3 to 7 carbon atoms,
or a pharmaceutically acceptable acid addition salt thereof.

2. The compound as defined in claim 1, where Y is hydrogen.

3. The compound as defined in claim 1, where X is hydrogen or halogen.

4. The compound as defined in claim 1, where X is hydrogen or fluorine.

5. The compound as defined in claim 1, where R$_1$ is loweralkyl.

6. The compound as defined in claim 1, where R$_2$ is hydrogen or methyl.

7. The compound as defined in claim 1, where R$_1$ is methyl, ethyl or propyl.

8. The compound as defined in claim 1, where Y is hydrogen, X is hydrogen or fluorine and R$_1$ is loweralkyl.

9. The compound as defined in claim 8, where R$_2$ is hydrogen or methyl.

10. The compound as defined in claim 8, where R$_1$ is methyl, ethyl or propyl.

11. The compound as defined in claim 1, which is 1-(methyl-4-pyridinylamino)-1H-indol-5-yl methylcarbamate.

12. The compound as defined in claim 1, which is 1-(methyl-4-pyridinylamino)-1H-indol-5-yl butylcarbamate.

13. The compound as defined in claim 1, which is 1-(methyl-4-pyridinylamino)-1H-indol-5-yl phenylmethylcarbamate.

14. The compound as defined in claim 1, which is 1-(propyl-4-pyridinylamino)-1H-indol-5-yl methylcarbamate.

15. The compound as defined in claim 1, which is 1-(propyl-4-pyridinylamino)-1H-indol-5-yl ethylcarbamate.

16. The compound as defined in claim 1, which is 1-(propyl-4-pyridinylamino)-1H-indol-5-yl propylcarbamate.

17. The compound as defined in claim 1, which is 1-(propyl-4-pyridinylamino)-1H-indol-5-yl isopropylcarbamate.

18. The compound as defined in claim 1, which is 1-(propyl-4-pyridinylamino)-1H-indol-5-yl butylcarbamate.

19. The compound as defined in claim 1, which is 1-(propyl-4-pyridinylamino)-1H-indol-5-yl heptylcarbamate.

20. The compound as defined in claim 1, which is 1-(propyl-4-pyridinylamino)-1H-indol-5-yl cyclohexylcarbamate.

21. The compound as defined in claim 1, which is 1-(propyl-4-pyridinylamino)-1H-indol-5-yl phenylmethylcarbamate.

22. The compound as defined in claim 1, which is 1-(propyl-4-pyridinylamino)-1H-indol-5-yl 4-chlorophenylmethylcarbamate.

23. The compound as defined in claim 1, which is 1-(propyl-4-pyridinylamino]-1H-indol-5-yl 2-phenylethylcarbamate.

24. The compound as defined in claim 1, which is (S)-(−)-1-(propyl-4-pyridinylamino)-1H-indol-5-yl 1-phenylethylcarbamate.

25. The compound as defined in claim 1, which is 1-(propyl-4-pyridinylamino)-1H-indol-5-yl dimethylcarbamate.

26. The compound as defined in claim 1, which is 1-(propyl-4-pyridinylamino)-1H-indol-5-yl piperidinylcarbamate.

27. The compound as defined in claim 1, which is 1-(propyl-4-pyridinylamino)-1H-indol-5-yl 1,2,3,4-tetrahydro-2-isoquinolinylcarbamate.

28. The compound as defined in claim 1, which is 1-[(3-fluoro-4-pyridinyl)propylamino]-1H-indol-5-yl methylcarbamate.

29. The compound as defined in claim 1, which is 1-[(3-fluoro-4-pyridinyl)propylamino]-1H-indol-5-yl butylcarbamate.

30. The compound as defined in claim 1, which is 1-[(3-fluoro-4-pyridinyl)propylamino]-1H-indol-5-yl heptylcarbamate.

31. The compound as defined in claim 1, which is 3-methyl-1-(propyl-4-pyridinylamino)-1H-indol-5-yl methylcarbamate.

32. The compound as defined in claim 1, which is 3-methyl-1-(propyl-4-pyridinylamino)-1H-indol-5-yl butylcarbamate.

33. The compound as defined in claim 1, which is 3-methyl-1-(propyl-4-pyridinylamino)-1H-indol-5-yl heptylcarbamate.

34. The compound as defined in claim 1, which is 3-methyl-1-(propyl-4-pyridinylamino)-1H-indol-5-yl phenylmethylcarbamate.

35. The compound as defined in claim 1, which is 3-methyl-(propyl-4-pyridinylamino)-1H-indol-5-yl 1,2,3,4-tetrahydro-2-isoquinolinylcarbamate.

36. The compound as defined in claim 1, which is 1-[(3-fluoro-4-pyridinyl)propylamino]-3-methyl-1H-indol-5-yl methylcarbamate.

37. The compound as defined in claim 1, which is 1-[(3-fluoro-4-pyridinyl)propylamino]-3-methyl-1H-indol-5-yl butylcarbamate.

38. The compound as defined in claim 1, which is 1-[(3-fluoro-4-pyridinyl)propylamino]-3-methyl-1H-indol-5-yl heptylcarbamate.

39. The compound as defined in claim 1, which is 1-[(3-fluoro-4-pyridinyl)propylamino]-3-methyl-1H-indol-5-yl phenylmethylcarbamate.

40. The compound as defined in claim 1, which is 1-[(3-fluoro-4-pyridinyl)propylamino]-3-methyl-1H-indol-5-yl 1,2,3,4-tetrahydro-2-isoquinolinylcarbamate.

41. A pharmaceutical composition comprising a compound as defined in claim 1 in an amount effective for alleviating a memory dysfunction characterized by a cholinergic deficit and a suitable carrier therefor.

42. A method of treating a patient in need of relief from a memory dysfunction characterized by a cholinergic deficit, which method comprises administering to such a patient an effective amount of a compound as defined in claim 1.

* * * * *